(12) United States Patent
Yeates et al.

(10) Patent No.: US 7,479,565 B2
(45) Date of Patent: Jan. 20, 2009

(54) PROCESS FOR THE PRODUCTION OF AN OLEFIN OXIDE, A 1,2-DIOL, A 1,2-DIOL ETHER, OR AN ALKANOLAMINE

(75) Inventors: Randall Clayton Yeates, Sugar Land, TX (US); Leonid Isaakovich Rubinstein, Houston, TX (US)

(73) Assignee: Shell Oil Company, Houston, TX (US)

( * ) Notice: Subject to any disclaimer, the term of this patent is extended or adjusted under 35 U.S.C. 154(b) by 587 days.

(21) Appl. No.: 11/154,143

(22) Filed: Jun. 16, 2005

(65) Prior Publication Data

US 2006/0009647 A1 Jan. 12, 2006

Related U.S. Application Data

(60) Provisional application No. 60/581,070, filed on Jun. 18, 2004.

(51) Int. Cl.
*C07D 301/10* (2006.01)

(52) U.S. Cl. .............. 549/536; 549/534; 422/189; 502/347; 564/477; 568/679; 568/867

(58) Field of Classification Search ........... 549/536; 502/347, 355; 564/477; 568/867, 679; 422/189
See application file for complete search history.

(56) References Cited

U.S. PATENT DOCUMENTS

| | | | | |
|---|---|---|---|---|
| 2,177,361 A | 10/1939 | Carter | ............ | 260/348 |
| 2,209,908 A | 7/1940 | Weiss | ............ | 23/234 |
| 2,294,383 A | 9/1942 | Carter | ............ | 260/348 |
| 3,808,153 A | 4/1974 | Chomitz et al. | ............ | 252/463 |
| 3,950,507 A | 4/1976 | Kuklina et al. | ............ | 423/626 |
| 4,318,896 A | 3/1982 | Schoonover | ............ | 423/628 |
| 4,379,134 A | 4/1983 | Weber et al. | ............ | 423/626 |
| 4,428,863 A | 1/1984 | Fry | ............ | 502/8 |
| 4,477,427 A | 10/1984 | Mátyasi et al. | ............ | 423/628 |
| 4,615,875 A | 10/1986 | Gonczy et al. | ............ | 423/626 |
| 4,731,350 A | 3/1988 | Boxhoorn et al. | ............ | 502/231 |
| 4,742,034 A | 5/1988 | Boxhoorn et al. | ............ | 502/231 |
| 4,761,394 A | 8/1988 | Lauritzen | ............ | 502/348 |
| 4,766,105 A | 8/1988 | Lauritzen | ............ | 502/348 |
| 4,822,900 A | 4/1989 | Hayden | ............ | 549/534 |
| 4,829,044 A | 5/1989 | Boxhoorn et al. | ............ | 502/348 |
| 4,845,296 A | 7/1989 | Ahmed et al. | ............ | 564/477 |
| 4,908,343 A | 3/1990 | Bhasin | ............ | 502/218 |
| 4,994,587 A | 2/1991 | Notermann et al. | ............ | 549/534 |
| 4,994,588 A | 2/1991 | Kapicak et al. | ............ | 549/534 |
| 4,994,589 A | 2/1991 | Notermann | ............ | 549/534 |
| 5,015,614 A | 5/1991 | Baird, Jr. et al. | ............ | 502/250 |
| 5,051,395 A | 9/1991 | Mitchell et al. | ............ | 502/348 |
| 5,063,195 A | 11/1991 | Jin et al. | ............ | 502/341 |
| 5,187,140 A | 2/1993 | Thorsteinson et al. | ............ | 502/348 |
| 5,248,557 A | 9/1993 | Jacobson | ............ | 428/404 |
| 5,380,697 A | 1/1995 | Matusz et al. | ............ | 502/348 |
| 5,538,709 A | 7/1996 | Mohri et al. | ............ | 423/625 |
| 5,612,267 A | 3/1997 | Bachelard et al. | ............ | 501/127 |
| 5,739,075 A | 4/1998 | Matusz | ............ | 502/302 |
| 5,780,656 A | 7/1998 | Rizkalla et al. | ............ | 549/534 |
| 6,203,773 B1 | 3/2001 | Easley et al. | ............ | 423/626 |
| 6,368,998 B1 | 4/2002 | Lockemeyer | ............ | 502/347 |
| 6,667,270 B2 | 12/2003 | Tanev | ............ | 502/208 |
| 2001/0046943 A1 | 11/2001 | Cheung et al. | ............ | 502/325 |
| 2003/0162984 A1* | 8/2003 | Lockemeyer et al. | ............ | 549/534 |
| 2006/0014971 A1 | 1/2006 | Yeates et al. | ............ | 549/534 |
| 2006/0047130 A1 | 3/2006 | Yeates et al. | ............ | 549/534 |
| 2006/0205962 A1 | 9/2006 | Rubinstein et al. | ............ | 549/534 |
| 2006/0258532 A1 | 11/2006 | Thorsteinson et al. | ............ | 502/347 |
| 2007/0111886 A1 | 5/2007 | Serafin et al. | ............ | 502/348 |

FOREIGN PATENT DOCUMENTS

| | | |
|---|---|---|
| EP | 003642 B1 | 7/1984 |
| EP | 244895 B1 | 11/1987 |
| EP | 266852 A1 | 5/1988 |
| EP | 327356 B1 | 8/1989 |
| EP | 352850 A1 | 1/1990 |
| EP | 425020 A1 | 5/1991 |
| EP | 429548 B1 | 6/1991 |

(Continued)

OTHER PUBLICATIONS

Journal of the American Chemical Society 60 (1938) pp. 309-316.

(Continued)

*Primary Examiner*—B. Dentz
*Assistant Examiner*—David E Gallis

(57) ABSTRACT

A process is provided for the epoxidation of an olefin comprising the steps of: contacting a feed comprising an olefin and oxygen with a catalyst comprising a silver component deposited on a fluoride-mineralized carrier; and producing a product mix comprising an olefin oxide, wherein the partial pressure of olefin oxide in the product mix is greater than about 60 kPa. A process is provided for the epoxidation of an olefin comprising the steps of: contacting a feed comprising an olefin and oxygen with a catalyst comprising a silver component and a high-selectivity dopant deposited on a fluoride-mineralized carrier; and producing a product mix comprising an olefin oxide, wherein the partial pressure of olefin oxide in the product mix is greater than about 20 kPa.

21 Claims, No Drawings

FOREIGN PATENT DOCUMENTS

| | | |
|---|---|---|
| EP | 0266015 | 12/1991 |
| EP | 480537 A1 | 4/1992 |
| EP | 496470 A1 | 7/1992 |
| EP | 0352850 | 1/1994 |
| EP | 679611 A1 | 11/1995 |
| WO | WO9915777 | 12/1990 |
| WO | WO9621619 | 7/1996 |
| WO | 00/15333 | 3/2000 |
| WO | 00/15334 | 3/2000 |
| WO | WO0015335 | 3/2000 |
| WO | WO0119763 A1 | 3/2001 |
| WO | WO2005023418 A1 | 3/2005 |
| WO | WO2006009756 A1 | 1/2006 |
| WO | WO2006028544 A2 | 3/2006 |
| WO | WO2006028940 | 3/2006 |
| WO | WO2006091478 | 8/2006 |

OTHER PUBLICATIONS

Kirk-Othmer Encyclopedia of Chemical Technology, 3$^{rd}$ edition, vol. 9, 1980, pp. 445-447.

Morey, George W., "The Properties of Glass", 2$^{nd}$ Edition, American Chemical Society Monograph Series, Reinhold Publishing Corp. (1954), pp. 25, 26, 35.

Supplemental Preliminary Amendment dated Jan. 12, 2007, for U.S. Appl. No. 10/573,694.

Third Supplemental Preliminary Amendment dated Feb. 23, 2007, for U.S. Appl. No. 10/573,694.

Second Supplemental Preliminary Amendment dated Jan. 19, 2007, for U.S. Appl. No. 10/573,694.

Second Supplemental Preliminary Amendment dated Jan. 19, 2007, for U.S. Appl. No. 10/567,178.

Supplmental Preliminary Amendment dated Jan. 12, 2007, for U.S. Appl. No. 10/567,178.

\* cited by examiner

PROCESS FOR THE PRODUCTION OF AN OLEFIN OXIDE, A 1,2-DIOL, A 1,2-DIOL ETHER, OR AN ALKANOLAMINE

This application claims the benefit of U.S. Provisional Application No. 60/581,070 filed Jun. 18, 2004 the entire disclosure of which is hereby incorporated by reference.

FIELD OF THE INVENTION

The present invention relates to a process for the production of an olefin oxide, a 1,2-diol, a 1,2-diol ether, or an alkanolamine.

BACKGROUND OF THE INVENTION

In olefin epoxidation, a feed containing an olefin and an oxygen source is contacted with a catalyst under epoxidation conditions. The olefin is reacted with oxygen to form an olefin oxide. A product mix results that contains olefin oxide and typically unreacted feed and combustion products.

The catalyst comprises silver, usually with one or more additional elements deposited therewith, on a carrier, typically an alpha-alumina carrier. The olefin oxide may be reacted with water to form a 1,2-diol, with an alcohol to form a 1,2-diol ether, or with an amine to form an alkanolamine. Thus, 1,2-diols, 1,2-diol ethers, and alkanolamines may be produced in a multi-step process initially comprising olefin epoxidation and then the conversion of the formed olefin oxide with water, an alcohol, or an amine.

The performance of the silver containing catalyst may be assessed on the basis of selectivity, activity, and stability of operation in the olefin epoxidation. The selectivity is the molar fraction of the converted olefin yielding the desired olefin oxide. As the catalyst ages, the fraction of the olefin reacted normally decreases with time. To maintain a desired constant level of olefin oxide production, the temperature of the reaction is increased. However, increasing the temperature causes the selectivity of the reaction to the desired olefin oxide to decrease. In addition, the equipment used in the reactor typically can tolerate temperatures only up to a certain level. Thus, it may become necessary to terminate the reaction when the reaction temperature reaches a temperature inappropriate for the reactor. Thus, the longer the selectivity can be maintained at a high level and the epoxidation can be performed at an acceptably low reaction temperature while maintaining an acceptable level of olefin oxide production, the longer the catalyst charge can be kept in the reactor and the more product is obtained. Stability refers to how the selectivity and/or activity of the process changes during the time a charge of catalyst is being used, i.e., as more olefin oxide is produced.

At any given time, the selectivity of a process is also dependent on the level of olefin oxide production. As the level of olefin oxide production, which is conveniently measured by the olefin oxide partial pressure in the product mix or mole percentage of olefin oxide in the product mix (i.e., at the reactor outlet), increases, the selectivity of the process decreases. Because of this, typical commercial olefin epoxidation processes are run at relatively low olefin oxide partial pressures, at the sacrifice of potential plant productivity.

Modern silver-based catalysts may comprise, in addition to silver, one or more high-selectivity dopants, such as components comprising rhenium, tungsten, chromium, or molybdenum. High-selectivity catalysts are disclosed, for example, in U.S. Pat. No. 4,761,394 and U.S. Pat. No. 4,766,105. U.S. Pat. No. 4,766,105 and U.S. Pat. No. 4,761,394 disclose that rhenium may be employed as a further component in the silver containing catalyst with the effect that the initial, peak selectivity of the olefin epoxidation is increased.

Depending upon the catalyst used and the parameters of the olefin epoxidation process, the time required to reach the initial, peak selectivity, that is the highest selectivity reached in the initial stage of the process, may vary. For example, the initial, peak selectivity of a process may be achieved after only 1 or 2 days of operation or may be achieved after as much as, for example, 1 month of operation. Working examples given in these US patents show a trend towards a higher selectivity at higher rhenium levels up to about 3 mmole rhenium/kg catalyst, on a carrier having a surface area of 0.42 $m^2/g$. EP-A-352850 also teaches that the then newly developed catalysts, comprising silver supported on alumina carrier, promoted with alkali metal and rhenium components have a very high selectivity.

Not withstanding the improvements already achieved, there is a desire to further improve the performance of olefin epoxidation catalysts, in particular, to increase the level of olefin oxide production without sacrificing the selectivities achievable with the use of the catalysts.

SUMMARY OF THE INVENTION

The present invention relates to a process for the production of an olefin oxide, a 1,2-diol, a 1,2-diol ether, or an alkanolamine.

The invention provides a process for the epoxidation of an olefin comprising the steps of contacting a feed comprising an olefin and oxygen with a catalyst comprising a silver component deposited on a fluoride-mineralized carrier; and producing a product mix comprising an olefin oxide, wherein the partial pressure of olefin oxide in the product mix is greater than about 60 kPa. In preferred embodiments, amongst others, the catalyst additionally comprises a high-selectivity dopant. In preferred embodiments, amongst others, the catalyst additionally comprises a Group IA metal component.

The invention provides a process for the epoxidation of an olefin comprising the steps of contacting a feed comprising an olefin and oxygen with a catalyst comprising a silver component and a high-selectivity dopant deposited on a fluoride-mineralized carrier; and producing a product mix comprising an olefin oxide, wherein the partial pressure of olefin oxide in the product mix is greater than about 20 kPa. In preferred embodiments, amongst others, the high-selectivity dopant comprises a rhenium component. In preferred embodiments, amongst others, the catalyst additionally comprises a Group IA metal component. In preferred embodiments, amongst others, the partial pressure of olefin oxide in the product mix is greater than about 40 kPa. In preferred embodiments, amongst others, the process exhibits a selectivity to the olefin oxide greater than 85%, preferably greater than 87%, more preferably greater than about 89%, and even more preferably greater than about 90%.

The invention also provides a process for the production of a 1,2-diol, a 1,2-diol ether, or an alkanolamine comprising converting an olefin oxide into the 1,2-diol, the 1,2-diol ether, or the alkanolamine, wherein the olefin oxide has been obtained by a process for the epoxidation of an olefin comprising reacting the olefin with oxygen in accordance with this invention.

The features and advantages of the present invention will be readily apparent to those skilled in the art upon reading the description of the invention that follows.

DETAILED DESCRIPTION OF THE INVENTION

The present invention relates to a process for the production of an olefin oxide, a 1,2-diol, a 1,2-diol ether, or an alkanolamine.

The invention provides a process for the epoxidation of an olefin in which an olefin and oxygen are contacted in the presence of a carrier supported catalyst and under epoxidation conditions to form an olefin oxide.

When a process for the epoxidation of an olefin is conducted using a catalyst comprising a silver component deposited on a fluoride-mineralized carrier, the process may be conducted at increasing levels of olefin oxide production without the expected loss in selectivity. The decrease in selectivity that would be expected as the level of olefin oxide production is increased may be at least partially offset by conducting the process using a catalyst comprising a silver component deposited on a fluoride-mineralized carrier. In preferred embodiments, the catalyst may additionally comprise a high-selectivity dopant. In preferred embodiments, the high-selectivity dopant comprises a rhenium component. In preferred embodiments, the catalyst may additionally comprise a Group IA metal component.

Fluoride-Mineralized Carrier

Fluoride-mineralized carriers are obtained by the incorporation of fluorine into the carrier. For purposes of the present invention, fluoride-mineralized carriers are obtained by combining alpha-alumina or alpha-alumina precursor(s) with a fluorine-containing species that is capable of liberating fluoride, typically as hydrogen fluoride, when the combination is calcined, and calcining the combination. Prior to calcining, the combination may be formed into formed bodies, for example by extrusion or spraying. Preferably, calcination is conducted at less than about 1,200° C., more preferably less than 1,100° C. Preferably, calcinations is conducted at greater than about 900° C., more preferably greater than about 1,000° C. If the temperature is sufficiently in excess of 1,200° C., the amount of fluoride liberated may be excessive and the morphology of the carrier may be detrimentally affected.

Within these limitations, the manner by which the fluorine-containing species is introduced into the carrier is not limited, and those methods known in the art for incorporating a fluorine-containing species into a carrier (and those fluoride-mineralized carriers obtained therefrom) may be used for the present invention. For example, U.S. Pat. No. 3,950,507 and U.S. Pat. No. 4,379,134 disclose methods for making fluoride-mineralized carriers and are hereby incorporated by reference.

In certain embodiments, the fluoride-mineralized carriers may have, and preferably do have, a particulate matrix having a morphology characterizable as lamellar or platelet-type, which terms are used interchangeably. As such, particles having in at least one direction a size greater than about 0.1 micrometers have at least one substantially flat major surface. Such particles may have two or more flat major surfaces. In alternative embodiments of this invention, carriers may be used which have said platelet-type structure and which have been prepared by a method other than the fluoride-mineralization methods described herein.

A suitable procedure for incorporating a fluorine-containing species into a carrier involves adding a fluorine-containing species to alpha-alumina or an alpha-alumina precursor(s). The alpha-alumina precursors mentioned herein are those species capable of being converted to alpha-alumina upon calcination. The alpha-alumina precursors include hydrated aluminas, such as boehmite, pseudoboehmite, and gibbsite, as well as transition aluminas, such as the chi, kappa, gamma, delta, theta, and eta aluminas.

If a hydrated alumina is used, a fluorine-containing species may suitably be added to the hydrated alumina with the combination then made into formed bodies, such as by extrusion or spraying. The hydrated alumina is then converted to alpha-alumina by calcining the formed bodies. Preferably, the calcination is conducted at less than about 1,200° C. During the calcination, fluoride is liberated. Similarly, a fluorine-containing species may suitably be added to a transition alumina, such as gamma alumina, or to a combination of transition alumina and hydrated alumina. The combination is made into formed bodies and calcined, as before.

In another suitable method, a fluorine-containing species may be added to formed bodies of alpha-alumina or an alpha-alumina precursor(s) or mixtures thereof. The formed bodies are then subjected to calcination. In another suitable method, the fluorine-containing species may be added to the carrier after calcination, i.e., after formation of alpha-alumina. In such a method, the fluorine-containing species may conveniently be incorporated in the same manner as silver and other promoters, e.g., by impregnation, typically vacuum impregnation.

As previously explained, calcination is preferably conducted at less than about 1,200° C. The present invention, however, is independent of the manner by which calcination is conducted. Thus, variations in calcining known in the art, such as holding at one temperature for a certain period of time and then raising the temperature to a second temperature over the course of a second period of time, are contemplated by the present invention.

The addition of the fluorine-containing species may be by any known method. In one such suitable method, the alpha-alumina or alpha-alumina precursor(s) is treated with a solution containing a fluorine-containing species. The combination is co-mulled and converted into formed bodies. Similarly, formed bodies may be subjected to vacuum impregnation with a solution containing a fluorine-containing species. Any combination of solvent and fluorine-containing species that results in the presence of fluoride ions in solution may be used in accordance with such a method.

Fluorine-containing species that may be used in accordance with this invention are those species that when incorporated into a carrier in accordance with this invention are capable of liberating fluoride, typically in the form of hydrogen fluoride, when calcined, preferably at less than about 1,200° C. Preferred fluorine-containing species are capable of liberating fluoride when calcining is conducted at a temperature of from about 900° C. to about 1,200° C. Such fluorine-containing species known in the art may be used in accordance with this invention. Suitable fluorine-containing species include organic and inorganic species. Suitable fluorine-containing species include ionic, covalent, and polar covalent compounds. Suitable fluorine-containing species include $F_2$, aluminum trifluoride, ammonium fluoride, hydrofluoric acid, and dichlorodifluoromethane.

The fluorine-containing species is typically used in an amount such that a catalyst comprising silver deposited on the fluoride-mineralized carrier, when used in a process for the epoxidation of an olefin as defined in connection with this invention, exhibits a selectivity that is greater than a comparable catalyst deposited on an otherwise identical, non-fluoride-mineralized carrier that does not have a lamellar or platelet-type morphology, when used in an otherwise identical process. Typically, the amount of fluorine-containing species added to the carrier is at least about 0.1 percent by weight and typically no greater than about 5.0 percent by weight, calculated as the weight of elemental fluorine used relative to the weight of the carrier material to which the fluorine-containing species is being incorporated. Preferably, the fluorine-containing species is used in an amount no less than about 0.2 percent by weight, more preferably no less than about 0.25 percent by weight. Preferably, the fluorine-containing species is used in an amount no more than about 3.0 percent by weight, more preferably no more than about 2.5 percent by weight. These amounts refer to the amount of the species as initially added and do not necessarily reflect the amount that may ultimately be present in the finished carrier.

Other than being fluoride-mineralized as described above, the carriers that may be used in accordance with this invention are not generally limited. Typically, suitable carriers comprise at least 85 percent by weight, more typically 90 percent by weight, in particular 95 percent by weight alpha-alumina, frequently up to 99.9 percent by weight alpha-alumina, based on the weight of the carrier. The carrier may additionally comprise, silica, alkali metal, for example sodium and/or potassium, and/or alkaline earth metal, for example calcium and/or magnesium.

Suitable carriers are also not limited with respect to surface area, water absorption, or other properties. The surface area of the carrier may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 10 m$^2$/g, preferably at most 5 m$^2$/g, and in particular at most 3 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha-alumina carriers optionally comprising in addition silica, alkali metal and/or alkaline earth metal, provide improved performance and stability of operation. However, when the surface area is very large, carriers tend to have lower crush strength.

The water absorption of the carrier may suitably be at least 0.2 g/g, preferably at least 0.3 g/g, relative to the weight of the carrier. The water absorption of the carrier may suitably be at most 0.8 g/g, preferably at most 0.7 g/g, relative to the weight of the carrier. A higher water absorption may be in favor in view of a more efficient deposition of silver and further elements, if any, on the carrier by impregnation. However, at higher water absorptions, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

Catalyst

In accordance with the present invention, the catalyst comprises a silver component deposited on the previously described fluoride-mineralized carrier. The catalyst may additionally comprise, and preferably does comprise, a high-selectivity dopant. The catalyst may additionally comprise, and preferably does comprise, a Group IA metal component.

The catalyst comprises silver as a catalytically active component. Appreciable catalytic activity is typically obtained by employing silver in an amount of at least 10 g/kg, calculated as the weight of the element relative to the weight of the catalyst. Preferably, the catalyst comprises silver in a quantity of from 50 to 500 g/kg, more preferably from 100 to 400 g/kg, for example 105 g/kg, or 120 g/kg, or 190 g/kg, or 250 g/kg, or 350 g/kg.

The catalyst may comprise, in addition to silver, one or more high-selectivity dopants. Catalysts comprising a high-selectivity dopant are known from U.S. Pat. No. 4,761,394 and U.S. Pat. No. 4,766,105, which are incorporated herein by reference. The high-selectivity dopants may comprise, for example, components comprising one or more of rhenium, molybdenum, chromium, and tungsten. The high-selectivity dopants may be present in a total quantity of from 0.01 to 500 mmole/kg, calculated as the element (for example, rhenium, molybdenum, tungsten, and/or chromium) on the total catalyst. Rhenium, molybdenum, chromium, or tungsten may suitably be provided as an oxide or as an oxyanion, for example, as a perrhenate, molybdate, and tungstate, in salt or acid form. The high-selectivity dopants may be employed in the invention in a quantity sufficient to provide a catalyst having a content of high-selectivity dopant as disclosed herein. of special preference are catalysts that comprise a rhenium component, and more preferably also a rhenium co-promoter, in addition to silver. Rhenium co-promoters are selected from tungsten, molybdenum, chromium, sulfur, phosphorus, boron, compounds thereof, and mixtures thereof.

When the catalyst comprises a rhenium component, rhenium may typically be present in a quantity of at least 0.1 mmole/kg, more typically at least 0.5 mmole/kg, and preferably at least 1.0 mmole/kg, in particular at least 1.5 mmole/kg, calculated as the quantity of the element relative to the weight of the catalyst. Rhenium is typically present in a quantity of at most 5.0 mmole/kg, preferably at most 3.0 mmole/kg, more preferably at most 2.0 mmole/kg, in particular at most 1.5 mmole/kg. Again, the form in which rhenium is provided to the carrier is not material to the invention. For example, rhenium may suitably be provided as an oxide or as an oxyanion, for example, as a rhenate or perrhenate, in salt or acid form.

If present, preferred amounts of the rhenium co-promoter are from 0.1 to 30 mmole/kg, based on the total amount of the relevant elements, i.e., tungsten, molybdenum, chromium, sulfur, phosphorus and/or boron, relative to the weight of the catalyst. The form in which the rhenium co-promoter is provided to the carrier is not material to the invention. For example, the rhenium co-promoter may suitably be provided as an oxide or as an oxyanion, in salt or acid form.

Suitably, the catalyst may also comprise a Group IA metal component. The Group IA metal component typically comprises one or more of lithium, potassium, rubidium, and cesium. Preferably the Group IA metal component is lithium, potassium and/or cesium. Most preferably, the Group IA metal component comprises cesium or cesium in combination with lithium. Typically, the Group IA metal component is present in the catalyst in a quantity of from 0.01 to 100 mmole/kg, more typically from 0.50 to 50 mmole/kg, more typically from 1 to 20 mmole/kg, calculated as the total quantity of the element relative to the weight of the catalyst. The form in which the Group IA metal is provided to the carrier is not material to the invention. For example, the Group IA metal may suitably be provided as a hydroxide or salt.

As used herein, the quantity of Group IA metal present in the catalyst is deemed to be the quantity in so far as it can be extracted from the catalyst with de-ionized water at 100° C. The extraction method involves extracting a 10-gram sample of the catalyst three times by heating it in 20 mL portions of de-ionized water for 5 minutes at 100° C. and determining in the combined extracts the relevant metals by using a known method, for example atomic absorption spectroscopy.

The preparation of the catalysts, including methods for incorporating silver, high-selectivity dopant, and Group IA metal is known in the art and the known methods are applicable to the preparation of the catalyst that may be used in accordance with the present invention. Methods of preparing the catalyst include impregnating the carrier with a silver compound and performing a reduction to form metallic silver particles. Reference may be made, for example, to U.S. Pat. No. 5,380,697, U.S. Pat. No. 5,739,075, EP-A-266015, U.S. Pat. No. 6,368,998, WO-00/15333, WO-00/15334 and WO-00/15335, which are incorporated herein by reference.

The reduction of cationic silver to metallic silver may be accomplished during a step in which the catalyst is dried, so that the reduction as such does not require a separate process step. This may be the case if the impregnation solution comprises a reducing agent, for example, an oxalate. Such a drying step is suitably carried out at a reaction temperature of at most 300° C., preferably at most 280° C., more preferably at most 260° C., and suitably at a reaction temperature of at least 200° C., preferably at least 210° C., more preferably at least 220° C., suitably for a period of time of at least 1 minute, preferably at least 2 minutes, and suitably for a period of time of at most 60 minutes, preferably at most 20 minutes, more preferably at most 15 minutes, and more preferably at most 10 minutes.

Epoxidation Process

Although the present epoxidation process may be carried out in many ways, it is preferred to carry it out as a gas phase process, i.e., a process in which the feed is contacted in the gas phase with the catalyst which is present as a solid material, typically in a fixed bed under epoxidation conditions. Epoxidation conditions are those combinations of conditions, notably temperature and pressure, under which epoxidation will occur. Generally, the process is carried out as a continuous process, such as the typical commercial process involving fixed-bed, tubular reactors.

The typical commercial reactor has a plurality of elongated tubes typically situated parallel to each other. While the size and number of tubes may vary from reactor to reactor, a typical tube used in a commercial reactor will have a length between 4-15 meters and an internal diameter between 1-7 centimeters. Suitably, the internal diameter is sufficient to accommodate the catalyst. In particular, the internal diameter of the tube is sufficient to accommodate the formed bodies of the carrier. Frequently, in commercial scale operation, the process of the invention may involve a quantity of catalyst which is at least 10 kg, for example at least 20 kg, frequently in the range of from $10^2$ to $10^7$ kg, more frequently in the range of from $10^3$ to $10^6$ kg.

The olefin used in the present epoxidation process may be any olefin, such as an aromatic olefin, for example styrene, or a di-olefin, whether conjugated or not, for example 1,9-decadiene or 1,3-butadiene. An olefin mixture may be used. Typically, the olefin is a mono-olefin, for example 2-butene or isobutene. Preferably, the olefin is a mono-α-olefin, for example 1-butene or propylene. The most preferred olefin is ethylene.

The olefin concentration in the feed may be selected within a wide range. Typically, the olefin concentration in the feed will be at most 80 mole-%, relative to the total feed. Preferably, it will be in the range of from 0.5 to 70 mole-%, in particular from 1 to 60 mole-%, on the same basis. As used herein, the feed is considered to be the composition that is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (typically at least 95 mole-%) oxygen is employed as the source of the oxidizing agent. Presently most epoxidation plants are oxygen-based and this is a preferred embodiment of the present invention.

The oxygen concentration in the feed may be selected within a wide range. However, in practice, oxygen is generally applied at a concentration that avoids the flammable regime. Typically, the concentration of oxygen applied will be within the range of from 1 to 15 mole-%, more typically from 2 to 12 mole-% of the total feed.

In order to remain outside the flammable regime, the concentration of oxygen in the feed may be lowered as the concentration of the olefin is increased. The actual safe operating ranges depend, along with the feed composition, on the reaction conditions, such as the reaction temperature and the pressure.

An organic halide may be present in the feed as a reaction modifier for increasing the selectivity, suppressing the undesirable oxidation of olefin or olefin oxide to carbon dioxide and water, relative to the desired formation of olefin oxide. Acceptable organic halides include organic bromides and organic chlorides, with organic chlorides being more preferred. Preferred organic halides are chlorohydrocarbons or bromohydrocarbons and are preferably selected from the group of methyl chloride, ethyl chloride, ethylene dichloride, ethylene dibromide, vinyl chloride, or a mixture thereof. The most preferred organic halides are ethyl chloride and ethylene dichloride.

The organic halides are generally effective as a reaction modifier when used in low concentration in the feed, for example up to 0.01 mole-%, relative to the total feed. In particular when the olefin is ethylene, it is preferred that the organic halide is present in the feed at a concentration of at most $50 \times 10^{-4}$ mole-%, in particular at most $20 \times 10^{-4}$ mole-%, more in particular at most $15 \times 10^{-4}$ mole-%, relative to the total feed, and preferably al least $0.2 \times 10^{-4}$ mole-%, in particular at least $0.5 \times 10^{-4}$ mole-%, more in particular at least $1 \times 10^{-4}$ mole-%, relative to the total feed.

In addition to the olefin, oxygen, and the organic halide, the feed may contain one or more optional components, for example carbon dioxide, inert gases, and saturated hydrocarbons. Carbon dioxide is a by-product in the epoxidation process, and may be present in the feed as a result of being recovered from the product mix together with unconverted olefin and/or oxygen and recycled. Typically, a concentration of carbon dioxide in the feed in excess of 25 mole-%, preferably in excess of 10 mole-%, relative to the total feed, is avoided. For the present invention, a concentration of carbon dioxide lower than about 2 mole-% is preferred. More preferred is a concentration of carbon dioxide lower than about 1 mole-%, and even more preferred is a concentration of carbon dioxide lower than about 0.75 mole-%. Frequently, when practicing the present invention, the concentration of carbon dioxide is at least 0.1 mole-%, and more frequently the concentration of carbon dioxide is at least 0.3 mole-%. Most preferred is a concentration of carbon dioxide between about 0.50 mole-% and 0.75 mole-%. At a low concentration of carbon dioxide, the process produces the olefin oxide at a higher selectivity than at a high concentration of carbon dioxide. Moreover, when operating at a low concentration of carbon dioxide, the process exhibits improved stability, including improved stability in selectivity and/or improved stability in activity.

Inert gases, for example nitrogen or argon, may be present in the feed in a concentration of from 30 to 90 mole-%, typically from 40 to 80 mole-%, relative to the total feed. The feed may contain saturated hydrocarbons. Suitable saturated hydrocarbons are methane and ethane. If saturated hydrocarbons are present, they may be present in a quantity of up to 80 mole-%, relative to the total feed, in particular up to 75 mole-%. Frequently they may be present in a quantity of at least 30 mole-%, more frequently at least 40 mole-%. Saturated hydrocarbons may be added to the feed in order to increase the oxygen flammability limit.

The epoxidation process may be carried out using epoxidation conditions, including temperature and pressure, selected from a wide range. Preferably the reaction temperature is in the range of from 150 to 340° C., more preferably in the range of from 180 to 325° C. The reaction temperature may be increased gradually or in a plurality of steps, for example in steps of from 0.1 to 20° C., in particular 0.2 to 10° C., more in particular 0.5 to 5° C. The total increase in the reaction temperature may be in the range of from 10 to 140° C., more typically from 20 to 100° C. The reaction temperature may be increased typically from a level in the range of from 150 to 300° C., more typically from 200 to 280° C., when a fresh catalyst is used, to a level in the range of from 230 to 340° C., more typically from 240 to 325° C., when the catalyst has decreased in activity due to ageing.

The epoxidation process is preferably carried out at a reactor inlet pressure in the range of from 1,000 to 3,500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a fixed catalyst bed, the GHSV is in the range of from 1,500 to 10,000 Nl /(l.h).

An advantage of the present invention is that the process may be conducted at higher levels of olefin oxide production while at least partially offsetting the concomitant reduction in selectivity expected with increased olefin oxide production. As such, the process of the present invention is preferably conducted under higher olefin oxide production conditions. Preferably, the process of the present invention is conducted under conditions where the olefin oxide partial pressure in the product mix is greater than about 20 kPa. More preferably, olefin oxide partial pressure in the product mix is greater than about 30 kPa, and even more preferably greater than about 40 kPa. The olefin oxide partial pressure in the product mix is frequently at most about 70 kPa, more frequently at most about 60 kPa, and even more frequently at most about 50 kPa. In some embodiments, the olefin oxide partial pressure in the product mix may be as much as 60 kPa, frequently as much as 70 kPa. The term "product mix" as used herein is understood to refer to the product recovered from the outlet of an epoxidation reactor.

When operating at these olefin oxide production levels, the olefin epoxidation process using a catalyst comprising a silver component and a high-selectivity dopant, preferably comprising a rhenium component, deposited on a fluoride-mineralized carrier achieves initial, peak selectivities greater than 85%. Preferably, such a process achieves selectivities greater than 87%. More preferably, such a process achieves selectivities greater than 89%. Frequently, such a process achieves selectivities of greater than 90% and at most about 92%. Without being limited, it is believed that the advantages of the present invention may be due, at least in part, to a decrease in the occurrence of indirect combustion, i.e., the combustion of olefin and oxygen to the desired olefin oxide followed by the combustion of the olefin oxide with oxygen to carbon dioxide and water.

The olefin oxide produced may be recovered from the product mix by using methods known in the art, for example by absorbing the olefin oxide from a product mix in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, or an alkanolamine. The methods employed for such conversions are not limited, and those methods known in the art may be employed.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g., 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers is increased. The 1,2-diol ethers thus produced may be a di-ether, tri-ether, tetra-ether or a subsequent ether. Alternatively, 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise reacting the olefin oxide with an amine, such as ammonia, an alkyl amine, or a dialkylamine. Anhydrous or aqueous ammonia may be used. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic compounds mentioned herein, for example the olefins, 1,2-diols, 1,2-diol ethers, alkanolamines, and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e., carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLE 1

Fluoride Mineralized Carrier Preparation

An impregnation solution was made by dissolving 12.24 g of ammonium fluoride in 300 g of distilled water. The amount of ammonium fluoride was determined by:

$$F \times m_{alumina} \left[ \frac{\text{wt \% NH}_4\text{F}}{100 - \text{wt \% NH}_4\text{F}} \right]$$

where F is a factor that is at least 1.5. The amount of water was determined by:

$$F \times m_{alumina} \times \text{WABS}$$

where $m_{alumina}$ is the mass of the transition gamma-alumina starting material, wt % $NH_4F$ is the weight percent of ammonium fluoride used, and WABS is the water absorption (g $H_2O$/g alumina) of the transition alumina. The factor "F" is large enough to provide an excess of impregnation solution that allows the alumina to be completely submerged.

An extruded transition alumina that had been cut into individual cylindrical formed bodies was used. 150 grams of the transition alumina was evacuated to 20 mm Hg for 1 minute and the final impregnating solution was added to the transition alumina while under vacuum. The vacuum was released and the transition alumina was allowed to contact the liquid for 3 minutes. The impregnated transition alumina was then centrifuged at 500 rpm for 2 minutes to remove excess liquid. Impregnated transition alumina pellets were dried in flowing nitrogen at 120° C. for 16 hours.

The dried impregnated transition alumina was placed in a first high temperature alumina crucible. Approximately 50 g of calcium oxide was placed in a second high temperature alumina crucible. The high temperature alumina crucible that contained the impregnated transition alumina was placed into the second high temperature alumina crucible, which contained the calcium oxide, and was then covered with a third high temperature alumina crucible of smaller diameter than the second crucible, such that the impregnated transition alumina was locked in by the third crucible and the calcium oxide. This assembly was placed into a cool furnace. The temperature of the furnace was increased from room temperature to 800° C. over a period of 30 minutes. The assembly was then held at 800° C. for 30 minutes and thereafter heated to 1,200° C. over a period of 1 hour. The assembly was then held at 1,200° C. for 1 hour. The furnace was then allowed to cool and the alumina removed from the assembly.

The carrier thus obtained (Carrier A) had the properties described in Table 1. The carrier had a particulate matrix having a morphology characterizable as lamellar or platelet-type.

TABLE 1

Properties of Carrier Support

| Properties | Carrier A |
|---|---|
| Water Absorption (g/g) | 0.59 |
| Surface Area (m²/g) | 0.71 |

EXAMPLE 2

Catalyst Preparation

This describes the preparation of a stock silver impregnation solution used for impregnating carrier materials as described in the following examples.

In a 5-liter stainless steel beaker, 415 grams of reagent grade sodium hydroxide was dissolved in 2,340 mL of deionized water. The temperature of the solution was adjusted to about 50° C. In a 4-liter stainless steel beaker, 1,699 grams of silver nitrate was dissolved in 2,100 mL of deionized water. The temperature of the solution was adjusted to about 50° C. The sodium hydroxide solution was slowly added to the silver nitrate solution with stirring while the temperature was maintained at about 50° C. The resulting slurry was stirred for about 15 minutes. The pH of the solution was maintained at above 10 by the addition of NaOH solution as required. A washing procedure was used which included removing liquid by the use of a filter wand followed by the replacement of the removed liquid with an equivalent volume of deionized water. This washing procedure was repeated until the conductivity of the filtrate dropped below 90 micro-mho/cm. After the completion of the last wash cycle, 1,500 mL of deionized water was added and followed by the addition of 630 grams of oxalic acid dihydrate (4.997 moles) in increments of 100 grams while stirring and maintaining the solution at about 40° C. (±5° C.). The pH of the solution was monitored during the addition of the last 130 grams of oxalic acid dihydrate to ensure that it did not drop below 7.8 for an extended period of time. Water was removed from the solution with a filter wand and the slurry was cooled to less than 30° C. Slowly added to the solution was 732 grams of 92% ethylenediamine. The temperature was maintained below 30° C. during this addition. A spatula was used to manually stir the mixture until enough liquid was present to mechanically stir. The final solution was used as a stock silver impregnation solution for preparing catalysts.

The impregnation solution for preparing Catalyst A was made by mixing 95.2 grams of silver stock solution of specific gravity 1.546 g/cc with a solution of 0.0617 g of $NH_4ReO_4$ in ~2 g of 1:1 $EDA/H_2O$, 0.0287 g of ammonium metatungstate dissolved in ~2 g of 1:1 ammonia/water and 0.0.1268 g $LiNO_3$ dissolved in water. Additional water was added to adjust the specific gravity of the solution to 1.507 g/cc. The doped solution was mixed with 0.136 g of 44.62% CsOH solution. This final impregnating solution was used to prepare Catalyst A. 30 grams of Carrier A was evacuated to 20 mm Hg for 1 minute and the final impregnating solution was added to Carrier A while under vacuum, then the vacuum was released and the carrier allowed to contact the liquid for 3 minutes. The impregnated Carrier A was then centrifuged at 500 rpm for 2 minutes to remove excess liquid. Impregnated Carrier A pellets were placed in a vibrating shaker and dried in flowing air at 250° C. for 5 ½ minutes. The final Catalyst A composition was 18.3% Ag, 400 ppm Cs/g catalyst, 1.5 μmole Re/g catalyst, 0.75 μmole W/g catalyst, and 12 μmole Li/g catalyst.

EXAMPLE 3

Catalyst Testing

Catalyst A may be used to produce ethylene oxide from ethylene and oxygen. To do this, 3.9 g of crushed catalyst would be loaded into a stainless steel U-shaped tube. The tube is then immersed in a molten metal bath (heat medium) and the ends are connected to a gas flow system. The weight of catalyst used and the inlet gas flow rate are adjusted to give a gas hourly space velocity of 3,300 Nl/(l.h), as calculated for uncrushed catalyst. The gas flow would be adjusted to 16.9 Nl/h. The inlet gas pressure would be 1,370 kPa.

The gas mixture would be passed through the catalyst bed, in a "once-through" operation, during the entire test run including the start-up, would be 30% v ethylene, 8% v oxygen, 0.5% v carbon dioxide, 61.5% v nitrogen and 2.0 to 6.0 parts by million by volume (ppmv) ethyl chloride.

For catalyst A, the initial reactor temperature would be 180° C., which would be ramped up at a rate of 10° C. per hour to 225° C. and then adjusted so as to achieve a desired constant level of ethylene oxide production, conveniently measured as partial pressure of ethylene oxide at the reactor outlet or molar percent ethylene oxide in the product mix.

At an ethylene oxide production level of 27 kPa for ethylene oxide partial pressure, Catalyst A would be expected to provide an initial, peak selectivity greater than about 86%, indeed greater than about 89%, and as much as about 92%. At an ethylene oxide production level of 48 kPa for ethylene oxide partial pressure, Catalyst A would be expected to provide an initial, peak selectivity greater than about 85%, indeed greater than about 88%, and as much as about 91%.

An advantage of the present invention is that the expected loss of selectivity associated with higher ethylene oxide partial pressures is at least partially offset when the process is conducted using a catalyst deposited on a fluoride-mineralized carrier. Thus, at an ethylene oxide production level of 55 kPa for ethylene oxide partial pressure, Catalyst A would be expected to provide an initial, peak selectivity greater than about 84%, indeed greater than about 87%, and as much as about 90%. At an ethylene oxide production level of 70 kPa for ethylene oxide partial pressure, Catalyst A would be expected to provide an initial, peak selectivity greater than about 84%, indeed greater than about 86%, and as much as about 89%. A comparable catalyst prepared on a non-fluoride-mineralized carrier, not having a lamellar or platelet-type morphology, would be expected to provide lower selectivities at the same ethylene oxide production levels, and would also be expected to have a less favorable ageing performance than the catalyst used in the present invention.

We claim:

1. A process for the epoxidation of an olefin comprising the steps of:
   contacting a feed comprising an olefin and oxygen with a catalyst comprising a silver component deposited on a fluoride-mineralized carrier; and
   producing a product mix comprising an olefin oxide, wherein the partial pressure of olefin oxide in the product mix is greater than about 60 kPa.

2. A process as claimed in claim 1, wherein the catalyst additionally comprises a high-selectivity dopant.

3. A process as claimed in claim 2, wherein the high-selectivity dopant comprises a rhenium component.

4. A process as claimed in claim 1, wherein the catalyst additionally comprises Group IA metal component.

5. A process as claimed in claim 1, wherein the carrier comprises alpha-alumina.

6. A process as claimed in claim 1, wherein the olefin comprises ethylene.

7. A process for the epoxidation of an olefin comprising the steps of:
   contacting a feed comprising an olefin and oxygen with a catalyst comprising a silver component and a high-selectivity dopant deposited on a fluoride-mineralized carrier; and
   producing a product mix comprising an olefin oxide, wherein the partial pressure of olefin oxide in the product mix is greater than about 40 kPa.

8. A process as claimed in claim 7, wherein the high-selectivity dopant comprises a rhenium component.

9. A process as claimed in claim 8, wherein the catalyst additionally comprises a rhenium co-promoter.

10. A process as claimed in claim 7, wherein the catalyst additionally comprises a Group IA metal component.

11. A process as claimed in claim 7, wherein the process employs a fixed bed, tubular reactor.

12. A process as claimed in claim 7, wherein the partial pressure of olefin oxide is at most 70 kPa.

13. A process as claimed in claim 7, wherein the partial pressure of olefin oxide is from about 40 kPa to about 60 kPa.

14. A process as claimed in claim 7, wherein the carrier comprises alpha-alumina.

15. A process as claimed in claim 7, wherein the olefin comprises ethylene.

16. A process for the epoxidation of an olefin comprising the steps of:
   contacting a feed comprising an olefin and oxygen with a catalyst comprising a silver component deposited on a carrier having a particulate matrix having a lamellar or platelet-type morphology; and
   producing a product mix comprising an olefin oxide, wherein the partial pressure of olefin oxide in the product mix is greater than about 60 kPa.

17. A process as claimed in claim 16, wherein the lamellar or platelet-type morphology is such that particles having in at least one direction a size greater than 0.1 micrometer have at least one substantially flat major surface.

18. A process for the epoxidation of an olefin comprising the steps of:
   contacting a feed comprising an olefin and oxygen with a catalyst comprising a silver component and a high-selectivity dopant deposited on a carrier having a particulate matrix having a lamellar or platelet-type morphology; and
   producing a product mix comprising an olefin oxide, wherein the partial pressure of olefin oxide in the product mix is greater than about 40 kPa.

19. A process as claimed in claim 18, wherein the high selectivity dopant comprises a rhenium component and the catalyst additionally comprises a rhenium co-promoter.

20. A process as claimed in claim 18, wherein the lamellar or platelet-type morphology is such that particles having in at least one direction a size greater than 0.1 micrometer have at least one substantially flat major surface.

21. A process for the production of a 1,2-diol, a 1,2-diol ether or an alkanolamine comprising:
   contacting a feed comprising an olefin and oxygen with a catalyst comprising a silver component and a high-selectivity dopant deposited on a fluoride-mineralized carrier;
   producing a product mix comprising an olefin oxide, wherein the partial pressure of olefin oxide in the product mix is greater than about 40 kPa; and
   converting the olefin oxide from the product mix into the 1,2-diol, the 1,2-diol ether or the alkanolamine.

* * * * *